United States Patent [19]

Scholl et al.

[11] Patent Number: 4,652,517

[45] Date of Patent: Mar. 24, 1987

[54] METHODS FOR THE IN VITRO DETECTION AND IDENTIFICATION OF UNKNOWN PATHOGENS OR GENETIC ENTITIES

[75] Inventors: David R. Scholl; Joseph D. Jollick, both of Athens, Ohio

[73] Assignee: Diagnostic Research Limited Partnership, Athens, Ohio

[21] Appl. No.: 619,286

[22] Filed: Jun. 11, 1984

[51] Int. Cl.⁴ .................. C12Q 1/70; C12Q 1/68; C12N 1/06
[52] U.S. Cl. .................................. 435/5; 435/6; 435/259; 435/803; 935/77; 935/78
[58] Field of Search ............... 435/5, 6, 7, 803, 259; 436/63, 94, 501, 504; 935/77, 78; 252/156, 550

[56] References Cited

U.S. PATENT DOCUMENTS 4,358,535 11/1982 Falkow .................................... 435/5
4,407,942 10/1983 Birnboim ................................ 435/6

OTHER PUBLICATIONS

Moseley, S. L. et al, *J. Infect. Dis.*, vol. 145, No. 6, 1982, pp. 863–869.
Windholz, M. et al, *The Merck Index*, 10th edition, Merck & Co., Inc., N.J., 1983, p. 1204.

Primary Examiner—Robert J. Warden
Assistant Examiner—Jeremy Jay
Attorney, Agent, or Firm—Senniger, Powers, Leavitt and Roedel

[57] ABSTRACT

Methods for the detection and identification of unknown pathogens or genetic entities from samples suspected of containing the same involve the use of novel wicking techniques whereby sample DNA/RNA becomes readily available on a porous, inert, positively charged support in single stranded form for hybridization with a hybridization probe having a nucleotide sequence substantially complementary to a nucleotide sequence of the sample DNA/RNA. Such methods permit the detection and identification of unknown pathogens and genetic entities in a shorter period of time than that required by conventional methods. Lysis solutions for rapidly lysing bacterial cells without the aid of enzymes are also disclosed.

38 Claims, 13 Drawing Figures cloned genomic fragment

METHODS FOR THE IN VITRO DETECTION AND IDENTIFICATION OF UNKNOWN PATHOGENS OR GENETIC ENTITIES

BACKGROUND OF THE INVENTION

This invention relates to methods for detecting the presence of unknown pathogens or microorganisms and, more particularly, to in vitro methods for detecting the presence of unknown pathogens in a more rapid manner and through the employment of procedures which can be readily and reliably carried out in clinical microbiology laboratories.

A critical factor in the clinical management of infectious diseases lies in the establishment of the identity of the etiologic agent or pathogen responsible for the infection. In most instances, the identification of the infecting microbe is central in making decisions respecting the appropriate therapy to be utilized. In this regard, the attending physician necessarily places heavy reliance upon the clinical microbiology laboratory to provide the essential data required to initiate a rational regimen of treatment.

Factors comprising procedures currently used in detecting pathogens in clinical specimens include the time required for detection, inability to rapidly cultivate the infectious agent in all instances, and difficulties concerning cross reactivity of reagents when performing assays directly from clinical specimens or samples.

Conventionally, the primary basis for the identification of pathogenic bacteria involves the detection of a products resulting from the metabolism of the unknown organism (Lennette et al., Manual of Clinical Microbiology, 1974, Amer. Soc. for Microbiol.), e.g. the detection of various enzymatic capabilities of a microbe by identification of specific substrate utilization or formation of specific metabolic end products. In most instances, identity of the unknown organism is based on color changes in multiple separate reactions (as many as 20-30) in order to arrive at a species level identification. In all cases, considerable growth of the microorganism under defined conditions is required to permit accumulation of the substances to be detected. The tests employed heretofore undesirably require numerous reagents and media, are timeconsuming and also require a considerable degree of skill and training on the part of clinical laboratory personnel.

During the past twenty years or so, various systems have been devised in an effort to simplify and shorten the time involved in the process of microorganism identification (Nord et al., Med Microbiol. Immunol., 1974, 159:211-220; Sakazaki, Media Circle, 1975, 20:227-235; and Robertson et al., J. Clin. Microbiol., 1976, 3:421-424). However, these systems basically represent variations on the same theme and rely on the same basic principle of metabolic product detection.

Reference may be made to the following literature publications as being representative of the state of the art as regards the rapid identification of infectious agents or microorganisms. Totten et al., DNA Hybridization Technique for the Detection of *Neisseria gonorrhaeae* in Men with Urethritis, Abstracts, Amer. Soc. Microbiol., March, 1982, discloses a technique for detecting *Neisseria gonorrhaeae* in patient specimens using a modification of the DNA hybridization method with the gonococcal cryptic plasmid as the radiolabelled probe. Moseley et al., Identification of Enterotoxigenic *Escherichia coli* by Colony Hybridization Using Three Enterotoxin Gene Probes, J. Infect. Dis. 145:863-869, discloses the applicability and limitation of the DNA hybridization technique for identifying enterotoxigenic *Escherichia coli* (ETEC).

A series of abstracts (C87 to C95, Abstracts of Annual Meeting-1982, Amer. Soc. Microbiol.) discloses evaluations and comparisons of multi-tube metabolic product test systems (API). Other abstracts in this series (C120 to C123 and C125) disclose evaluations of an automated radiometric blood culture system ("Bactec", Johnston Laboratories, Inc.) which relies upon the detection of metabolic products. Still other abstracts in this series (C124 to C128) describe blood culture systems for the concentration and separation of bacteria from blood samples. Abstract C254 in this same series describes a two-step procedure for expediting the recovery of microorganisms from blood.

Recently, it has become possible to produce large amounts of DNA fragments specific for an etiologic agent utilizing recombinant DNA molecules. Once the specificity of any particular fragment(s) for a certain pathogen has been established empirically, this DNA fragment or probe can be used to detect the presence of that pathogen through the probe's ability to hybridize with its complementary nucleic acid sequence of the pathogen, i.e. through DNA-DNA hybridization or DNA-RNA hybridization in the case of infectious viral entities that contain RNA genomes. RNA probes may also be used.

The use of such DNA probes in a diagnostic method for the detection of pathogens is disclosed in Falkow et al. U.S. Pat. No. 4,358,535. This patent generally discloses a method in which clinical isolates are cultivated, expanding the number of microorganisms, the resulting colonies are lysed and the genome is denatured and then fixed. Alternatively, clinical samples containing the pathogen are deposited or spotted onto an inert support. The sample is then treated and lysed to liberate the DNA from microbes present in the sample and to fix the DNA in substantially single stranded form at the same site on the support where the sample was deposited. Subsequently, the single stranded DNA on the support is contacted with a labeled polynucleotide probe with a nucleotide sequence complementary to that of the pathogen under hybridizing conditions whereby hybridization of the probe to the single stranded DNA of the pathogen is diagnostic of the presence of the pathogen. The patent states that the lysis conditions are devised such that the cells or colonies do not migrate and their DNA remains affixed in place on the surface of the support where they were situated. The method disclosed requires several days for detection of the pathogen involved.

In a more recent paper by Falkow and others (Totten et al., J. Infect. Dis., 1983, 148:462), the DNA hybridization technique was applied to the detection of *Neisseria gonorrhaeae* in men with urethritis directly from clinical specimens. However, the technique requires at least three days of reaction time to detect bacteria directly in patient specimens and thus is not immediately applicable to the clinical laboratory.

Brautigam et al. (J. Clin. Microbiol., 1980, 12:226-234) describe a method of typing clinical isolates of herpes simplex virus using hybridization between unlabeled DNA from infected cultures and tritium-labeled virus DNA. While the procedure can be completed within a day, it requires expensive, elaborate equipment and is not readily adapted to the processing of several clinical samples at any one time. It also requires performance by one relatively experienced in nucleic acid chemistry.

Moseley et al. (J. Infect. Dis., 1980, 142:892–898) disclose a method for detecting large numbers of isolates of enterotoxigenic *Escherichia coli* in which radiolabeled fragments of DNA encoding the heat-labile or heat-stable toxins were used as hybridization probes for homologous DNA sequences in *E. coli* colonies grown and lysed in situ on nitrocellulose filters. This method is also time-consuming and requires several days for completion.

Brechot et al. (The Lancet, October 10, 1981, p. 765–767) describe the use of DNA-DNA hybridization in the detection of hepatitis B virus in liver and serum. The procedure described requires tissue biopsies, followed by DNA extraction and subsequent steps which take about 3 to 4 days to complete.

Berninger et al. (J. Med. Virol., 1982, 9:57–68) discloses an assay based on nucleic acid hybridization which detects and quantitates hepatitis B virus (HBV) DNA in particles present in serum. The assay employs the complete hepatitis B virus DNA as a probe and the times required to complete the assay are relatively lengthy.

Thus, while the principle of nucleic acid hybridization has been recognized and used in the detection of pathogens, a need continues to exist for a more rapid, practical and accurate method for detecting pathogens directly from clinical samples to enhance the usefulness of the service rendered by clinical microbiology laboratories.

SUMMARY OF THE INVENTION

Among the objects of the present invention may be noted the provision of a method for the in vitro detection and identification of an unknown genetic entity having a specific DNA/RNA nucleotide sequence; the provision of an improved method for the in vitro detection of the presence of an unknown pathogen directly from clinical samples such as body fluids, exudates or tissues; the provision of such a method which may be carried out more rapidly while providing reliable results; and the provision of a method of this type which effectively separates the reactive pathogen DNA and/or RNA for subsequent treatment with polynucleotide probes under conditions favoring hybridization of pathogen DNA and/or RNA sequences to complementary sequences in the DNA and/or RNA of the probes; and the provision of novel lysis solution for use in such methods. Other objects and features will be in part pointed out hereinafter.

Briefly, the present invention is directed to a method for the in vitro detection of the presence of an unknown pathogen in a clinical sample suspected of containing the pathogen which includes the steps of (a) lysing the pathogen in the sample with a lysis solution containing an alkali and an anionic or zwitterionic surface active agent to liberate the DNA/RNA of the pathogen into the lysis solution in single stranded form; (b) contacting the resulting lysis solution containing the pathogen lysate with a porous, inert, positively charged support having DNA/RNA-binding capacity whereby the lysis solution migrates by capillary action on the support and the pathogen DNA/RNA in single stranded form becomes affixed at areas on the support to which the pathogen DNA/RNA has migrated; (c) contacting the resulting support carrying the single stranded pathogen DNA/RNA with a hybridization probe having a nucleotide sequence substantially complementary to a nucleotide sequence of the pathogen DNA/RNA whereby through hybridization the DNA/RNA of the probe becomes bound substantially only to the DNA/RNA of the unknown pathogen; and (d) detecting the presence of the unknown pathogen by determining whether binding of the DNA/RNA of the probe to DNA/RNA of the unknown pathogen through hybridization has occurred.

More broadly, the invention provides an improvement in a method for the in vitro detection and identification of an unknown genetic entity having a specific DNA/RNA nucleotide sequence present in a sample suspected of containing the genetic entity wherein the DNA/RNA is liberated from the sample in single stranded form and deposited on a support, the improvement involving contacting a solution containing the liberated sample DNA/RNA, an alkali and an anionic or zwitterionic surface active agent with a porous, inert, positively charged support whereby the solution migrates by capillary action on the support and the sample DNA/RNA in single stranded form becomes affixed at areas on the support to which the sample DNA/RNA has migrated, contacting the resulting support carrying the fixed single stranded sample DNA/RNA with a hybridization probe having a nucleotide sequence substantially complementary to a nucleotide sequence of the sample DNA/RNA whereby through hybridization the DNA/RNA of the probe becomes bound substantially only to the DNA/RNA of the unknown sample, and detecting the presence of the unknown DNA/RNA by determining whether binding of the DNA/RNA of the probe to DNA/RNA of the unknown sample through hybridization has occurred.

The invention is also directed to other embodiments of such a method including additional steps or variations in the aforementioned steps. In another but less preferred aspect of the invention, the detection of an unknown pathogen in a clinical sample is achieved through a method involving specific pre-lysis of the clinical sample, lysis, deposition of the pathogen DNA/RNA on a porous, inert support followed by hybridization to detect the presence of the unknown pathogen. The invention further includes novel lysis solutions for use in rapidly lysing gram negative and gram positive bacterial cells and viruses or viral agents.

DESCRIPTION OF THE PREFERRED EMBODIMENT

Figure 1:
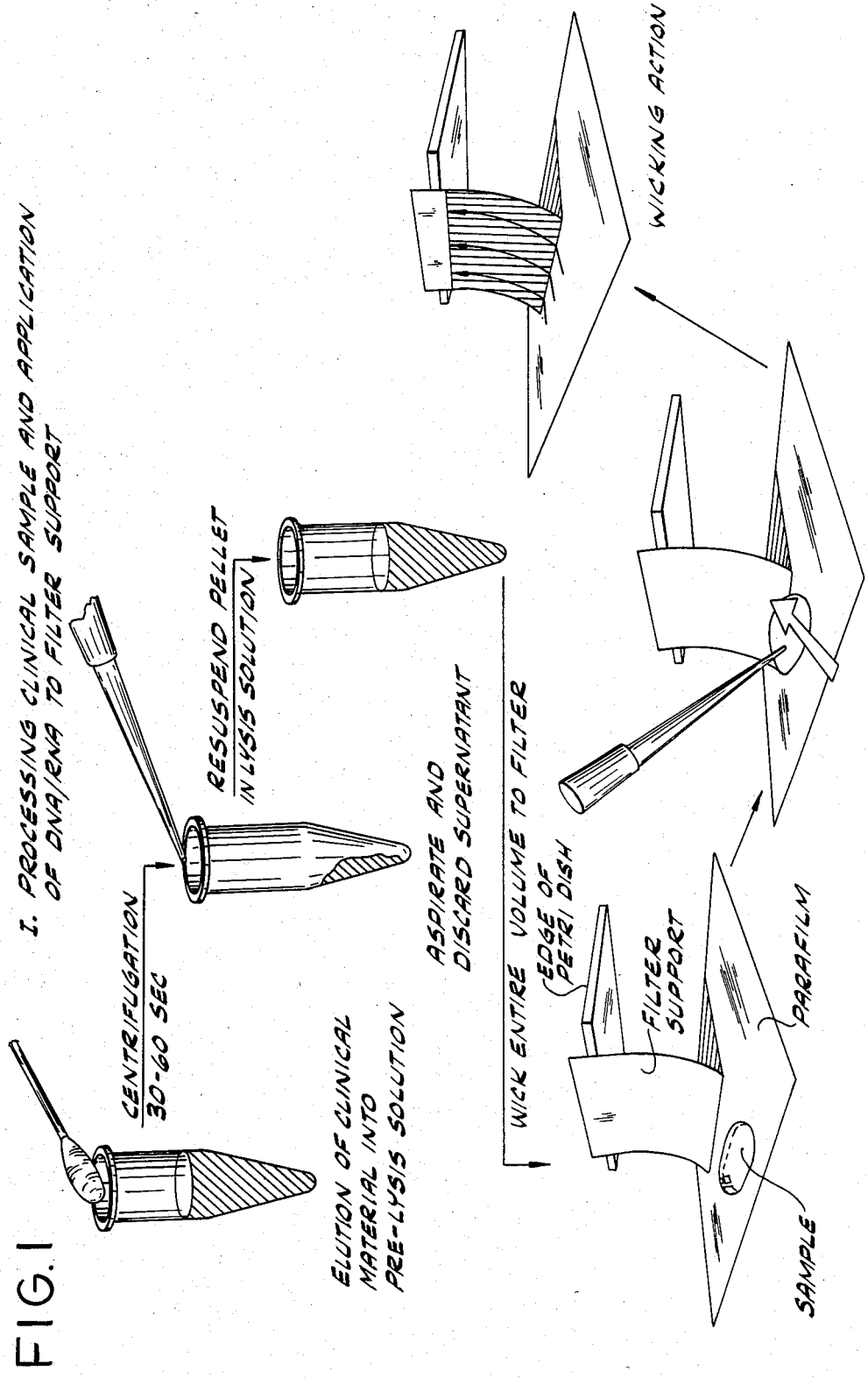
FIG. 1 is a schematic representation of the steps followed in processing a clinical sample and applying the sample DNA/RNA to a filter support using the method of the invention.

In accordance with the present invention, it has now been found that unknown pathogens contained in clinical samples may be accurately and more rapidly detected than heretofore possible through the employment of the novel methodology herein described. Utilizing the method of the present invention, cultivation of the pathogen is not required and the detection of an unknown pathogen directly from a clinical sample may be achieved in an overall time of as little as 1-2 hours in contrast to several days generally required heretofore with prior art methods. The method of the invention is directly applicable to several body fluids (e.g. blood samples, urine specimens, etc.), exudates and tissues that may vary widely in composition, and enables one to rapidly produce DNA/RNA directly from gram positive or gram negative bacteria, viral, and/or eukaryotic cell lysates in a form that is readily hybridizable.

After collection of a sample suspected of containing a pathogen or elution of the pathogen from a clinical isolate suspected of containing a pathogen, the method is carried out by treatment of the pathogen with a lysis solution containing an alkali and an anionic (e.g. sodium dodecyl sulfate) or zwitterionic surface active agent to effect lysis and denaturation of the pathogen DNA/RNA whereby the DNA/RNA of the pathogen is liberated into the lysis solution in single stranded form. The resulting DNA/RNA-containing lysis solution is then contacted with a porous, inert, positively charged support or matrix having DNA-binding capacity so that the lysis solution migrates by capillary action on the support or wicks onto the support and the pathogen DNA/RNA in single stranded form becomes irreversibly bound to the support at areas to which the pathogen DNA/RNA has migrated. We have found that upon so contacting the resulting DNA/RNA-containing lysis solution with such a positively charged support, a "wicking" action occurs whereby the anionic surface active agent first becomes bound to the support with the DNA/RNA of the pathogen being carried forward. As the wicking, spreading or migration continues, the lysis solution becomes relatively less concentrated with respect to the anionic surface active agent which is being continually bound to the support while becoming relatively more concentrated with respect to the pathogen DNA/RNA being carried forward. Thus, by such wicking action, the pathogen DNA/RNA is retained in the mobile phase until the anionic surface active agent is depleted to levels that are non-competing for reactive or binding sites on the positively charged support. Once the anionic surface active agent has been essentially or substantially fully deposited or bound to the support, the pathogen DNA/RNA becomes bound or affixed to the support in a more or less well-defined area or areas in single stranded form. The pathogen DNA/RNA is then ready for contacting with a hybridization probe and detection of the presence of an unknown pathogen is accomplished by using a probe that is specific for a particular etiologic agent or pathogen.

More broadly, we have found that the wicking action or migration described above may be usefully and effectively applied in the in vitro detection and identification of an unknown genetic entity having a specific DNA/RNA nucleotide sequence as well as in detecting and identifying pathogens in clinical samples. For example, the present invention may be used to diagnose specific genetic changes that result in genetic defects such as sickle-cell anemia, Tay Sachs disease and thalassemia. Additionally, the present invention could provide a very sensitive and rapid means to diagnose the inheritance of a defective gene. Although the exact nature of a specific genetic disorder may not be currently known, it is believed that the existence of an abnormal gene is the cause of the deleterious effect that is phenotypically displayed. Thus, the isolation and use of specific DNA probes that are complementary to the defective gene and not the normal gene may result in the early, in utero, diagnosis of the deleterious trait through the practice of the present invention.

Additionally, the advent of techniques enabling the insertion of functional genes into animal cells (Wagner et al., Proc. Natl. Acad Sci. U.S.A., 78:6376-6380. 1981) and plant cells (Shepard et al., Science, 219:683-688 , 1983) indicates the need for a method of rapidly determining the presence of a particular gene and the level of gene expression due to the presence of the inserted genetic material. The method of the present invention may be used to cause hybridization of a DNA/RNA probe to DNA/RNA molecules that are present and/or produced as a function of the introduction of the foreign genetic material into the recipient cell. Early detection following the introduction of genes into large animals could thereby be achieved and circumvent the need to delay identification of the transferred gene until a later stage of development, at which point the expression of the gene of interest would be monitored phenotypically at considerably larger expense.

While the methods of the invention thus have broad application, the invention is more particularly described hereinafter with reference to the detection of the presence of an unknown pathogen in a clinical sample suspected of containing the pathogen.

The clinical samples or specimens suspected of containing an unknown pathogen and to which the method of the present invention is applied may be any of the conventionally used samples such as blood, urine, sputum (e.g. throat swabs), vaginal swabs or stool samples. It is important for best results that there be maximum recovery of the starting material pathogen DNA/RNA, noting that in general, the clinical samples will usually contain a concentration of $10^5$–$10^6$ bacterial or pathogen cells. Thus, for example in the case of throat swabs, we have found that elution of the material present on the swab into a solution that does not harm the bacteria is adequate, although perhaps not the most efficient, in recovering bacterial cells. However, in addition to the unknown bacteria or pathogen, epithelial cells and other human cells (i.e. leukocytes responding to infection) will also be eluted along with other throat secretion products. Accordingly, without any selective separation of bacteria from human cells, there is likely to be a large amount of human DNA, protein and/or polysaccharides present. All of these products could compete with the bacterial or pathogen DNA of interest (e.g. group A Strep DNA) for binding sites on the porous, inert, positively charged support employed in our method if the clinical sample eluate is directly lysed thereby rendering our assay somewhat less sensitive. Preferably, but not essentially, therefore, the sample is first treated with a pre-lysis solution to remove a substantial portion of the competing or inhibiting components from the clinical eluate without lysing the pathogen. In most instances, such a pre-lysis treatment is not essential and the clinical sample can be eluted directly into a lysis solution and meaningful results are obtained. In this regard, it has been found that the aforementioned wicking phenomenon is useful in effecting separation of protein and extraneous polysaccharides since these materials tend to be deposited on the positively charged support with the anionic surface active agent rather than with the pathogen DNA/RNA and therefore do not effectively compete with the latter for sites on the support or for hybridization with the hybridization probe.

While not generally necessary, the clinical sample can be initially cultivated to produce more of the pathogen DNA/RNA and the cultivated pathogen may be collected by means of a bacteriological loop or speculum-like instrument.

Where a pre-lysis solution is employed to substantially eliminate or remove potential competitors/inhibitors from the clinical sample at the outset, we prefer to employ a solution containing a nonionic detergent, namely, purified saponin, at low concentration that results in the selective lysis of human cells. Typically, the pre-lysis solution may contain purified saponin, polypropylene glycol, polyanetholesulfonate, and disodium ethylenedinitrilo tetraacetate. The pre-lysis solution may also contain Tris buffer or other appropriate components such as enzymes.

After the clinical sample is eluted into a prelysis solution (if used) in a microcentrifuge tube, the pre-lysis/sample suspension is centrifuged for approximately 30–60 seconds and the supernatant is discarded. The remaining pellet, consisting of bacterial cells and debris, is resuspended in 50–100 1 of a lysis solution, the principal components of which are an alkali and an anionic or zwitterionic surface active agent, and then vigorously vortexed. A typical lysis solution consists of 126 mM sodium chloride, 8 mM ethylene diaminetetraacetate, 10 mM Tris, pH 7.5, and 2.35% sodium dodecyl sulfate (SDS), which is made 0.5 N in sodium hydroxide by the addition of 10 N sodium hydroxide to the above solution immediately prior to use. In lieu of sodium hydroxide, other alkalis such as potassium hydroxide or ammonium hydroxide may be utilized.

Sodium dodecyl sulfate (SDS) is the preferred surface active agent for use in the practice of the invention as the major component of the lysis solution. Not only does SDS, in conjunction with an alkali, function to liberate the DNA/RNA of the pathogen into the lysis solution in single stranded form but it also promotes the wickability or migratory action of the pathogen DNA/RNA when the resulting lysis solution is contacted with the porous, inert, positively charged support. Various other anionic or zwitterionic surface active agents known to those skilled in the art may also be employed and include sodium decyl sulfate, sodium tetradecyl sulfate, sodium dodecanoate, sodium cholate, sodium deoxycholate, lyso phosphatidylcholine, N-dodecyl betaine, N-tetradecyl betaine, N-hexyl-N,N-dimethyl-3-amino-1-propanesulfonate, N-octyl-N,N-dimethyl-3-ammonio-1-propenesulfonate, N-decyl-N,N-dimethyl-3-ammonio-1-propanesulfonate, N-dodecyl-N,N-dimethyl-3-ammonio-1-propanesulfonate, N-tetradecyl-N,N-dimethyl-3-ammonio-1-propanesulfonate and N-hexadecyl-N,N-dimethyl-3-ammoniol-propanesulfonate. Nonionic or cationic surface active agents or detergents are not useful for the purpose of the lysis solution.

The lysis solution containing an alkali and an anionic or zwitterionic surface active agent as the essential components constitutes yet another aspect of the invention. Heretofore, particularly in the case of gram positive cells, it has been regarded as essential and necessary to employ lysis solution containing enzymes such as pronase or lysozyme. Thus, lysis of gram positive bacteria, in particular Group A Streptococci, has always been performed using the enzymes pronase or lysozyme and then only after the bacterial cell walls have been weakened by growth in cell weakening agents such as bacitracin or penicillin for 45–60 minutes. As noted by Clewell, Microbiological Reviews, Vol. 45, p. 409–36, 1981, the streptococci are somewhat difficult to lyse and usually require extended incubation in lysozyme or other lytic enzymes before ionic detergents, such as sodium dodecyl sulfate and Sarkosyl, bring about lysis and even under these conditions, lysis is frequently incomplete. Similarly, in the case of gram negative bacteria, a combination of enzymes, such as lysozyme, detergents and pH conditions have been utilized.

In further accordance with the present invention, it has now been unexpectedly found that lysis of both gram negative and gram positive bacterial cells and viruses may be rapidly and effectively achieved without the aid of an enzyme through the use of a lysis solution containing an alkali such as sodium hydroxide and an anionic or zwitterionic surface active agent, such as sodium dodecyl sulfate or one of the other specific surface active agents previously enumerated, as the sole essential components. Such a lysis solution provides a rapid means for lysing bacterial cells and may be employed as a universal lysis solution to effect lysis of any infectious agent encountered in clinical specimens to which the method of the present invention may be applied. It is believed that the alkali functions as a denaturant and converts the sample DNA/RNA into single stranded form and that the surface active agent, in combination with the alkali lyses the cells and liberates the DNA/RNA therefrom.

The concentrations of alkali and anionic or zwitterionic surface active agent in the lysis solution may be varied, but it is generally preferred that the solution be 0.5N sodium hydroxide or other alkali and that the concentration of surface active agent be from about 0.5% to about 5.0% by weight, preferably about 2.35%. The lysis solution may also contain, as a specific example, 10 mM Tris pH 7.5, 126 mM NaCl and 8 mM ethylenediaminetetraacetic acid (EDTA), which amounts may also be varied within the practice of the invention. The use of sodium hydroxide and sodium dodecyl sulfate are especially preferred as the specific essential components of the lysis solution, it being noted that neither of these used alone is operative to effect lysis of the more difficult gram positive microorganisms.

While it is not, as indicated, essential to the achievement of lysis, the lysis solution may, if desired, also contain proteases, lipases, enzymes that hydrolyze polysaccharides, and lysostaphin.

Upon lysing the clinical sample or sample already treated with a pre-lysis solution, the pathogen DNA/RNA contained in the resulting lysis solution is in single stranded form ready for contacting with a porous, inert, positively charged support or matrix for fixing or binding of the pathogen DNA/RNA thereto. Preferred supports of this nature for use in the present invention include a nylon-based membrane marketed under the trade designation "Zetabind" by AMF Cuno, Microfiltration Products Division, Meriden, Ct. or a similar membrane marketed under the trade designation "GeneScreen" by New England Nuclear Corporation, Boston, Mass. Zetabind is composed of a nylon 66 matrix (a polyhexamethylene adipamine) modified by the introduction of numerous tertiary amino groups during manufacturing. It is inherently hydrophilic, flexible, exhibits wide solvent compatibility and exhibits a net positive charge due to the covalent modification of the nylon membrane structure. This inherent positive charge results in enhanced binding of anionic macromolecules. Zetabind is also available as Zeta Probe from Bio-Rad Laboratories, Richmond, Calif. GeneScreen is a similar positively charge support material. Less preferred but still useful in the practice of the invention as a positively charged support is nitrocellulose which is less highly positively charged than Zetabind or GeneScreen. Other porous, inert support materials such as fibrous materials coated or impregnated with positively charged resins or the like may also be used in carrying out our invention.

To demonstrate the phenomenon of wicking or migration and to determine where DNA would migrate if present in solutions of various SDS concentrations, DNA was seeded into lysis solutions containing 0.59, 1.18, 1.77 and 2.35% SDS. The solutions were wicked onto GeneScreen filter membrane supports and the resulting supports were subsequently hybridized to a DNA probe to determine the position of the DNA on the support relative to the solvent and SDS fronts. Autoradiography of the supports after hybridization showed that the majority of the reactive DNA was located just ahead of the SDS front, and that any remaining reactivity was randomly located at positions between the origin where wicking started and the SDS front. Additionally, reactivity increased as a function of SDS concentration, believed most likely due to a greater amount of DNA bound to the filter or as a result of the DNA existing in a more accessible, and thus hybridizable, form.

Wicking is preferably achieved by contacting the porous, inert, positively charged support with the lysis solution containing the pathogen DNA/RNA at an angle which may be, for example, a ninety degree angle from the horizontal or by contacting the support with the solution at a more or less vertical angle. Utilizing the wicking phenomenon, the increased reactivity achieved as a function of increased SDS or anionic surface active agent concentration is in direct contrast to the prior art methodology of spotting solutions containing pathogen DNA onto a small surface area of a support or filter membrane sustrate material such as nitrocellulose. Thus, we have found that when DNA was spotted onto a small, defined area of a GeneScreen support, for example, an increased concentration of SDS in the DNA sample resulted in less retention of substrate or target DNA, as evidenced by loss of radioactive DNA during filter binding assays under the aforementioned conditions. This indicates that the anionicity of SDS was competing with and inhibiting the polyanionic nature of DNA from interacting with the positively charged surface of the GeneScreen support.

The location of the pathogen DNA/RNA on the positively charged support achieved through the phenomenon of wicking in the practice of the invention and the increased reactivity observed with increased concentrations of SDS or other anionic surface active agent is indicative of the following. First, the majority or major amount of the reactive pathogen DNA/RNA is found slightly ahead of the SDS front on the support because it is a relatively weaker anion than SDS, and thus the DNA/RNA is retained in the mobile phase during wicking until the SDS is depleted to levels that are non-competing for reactive sites on the support. Secondly, increased SDS concentrations causes the SDS (in addition to the pathogen DNA/RNA) to migrate a further distance from the point of wicking origin on the support surface. The increase in DNA migration as a function of SDS concentration results in the reactive DNA being spread over a larger surface area, with the attendant result that more DNA molecules are bound to the support in single stranded form to produce a qualitatively better substrate for subsequent hybridization.

Once the pathogen DNA/RNA of the lysis solution has become bound to the porous, inert, positively charged support through wicking as described, the resulting support is preferably air dried for a brief period (e.g. 1 to 2 minutes) to irreversibly bind the pathogen DNA/RNA to the support. The support is then quickly dipped in Denhardt's Solution (0.02% each Ficoll (MW 400,000), polyvinylpyrrolidine (MW 360,000), bovine serum albumin (Fraction V) in $3 \times SSC$(0.15 M NaCl, 0.015 M sodium citrate pH 6.5)) to reduce the nonspecific binding of the hybridization probe to the support and to leach out the alkali from the lysis solution. The support is then ready to be contacted with a hybridization probe.

The hybridization probes used in the practice of the invention are based on the principle that in any well defined species of microorganism or pathogen, there are specific nucleotide sequences in the genetic material that are unique to that species and that these sequences can be detected by the technique of DNA-DNA hybridization (Parish, "Principles and Practice of Experiments with Nucleic Acids", Longman, London, 1972, pages 355–368) in which the reaction of a specific complementary DNA-DNA hybridization probe occurs with the DNA of an unknown microorganism thus revealing its identity. For example, unique DNA nucleotide sequences in the form of a hybridization probe isolated from the microorganism Staphylococcus aureus will react only with DNA found in lysates of that species.

The DNA-DNA hybridization probes used in the present invention are comprised of cloned polynucleotide fragments of genomic DNA of a known microorganism. The probes are characterized by having no substantial cross-reactivity with any microorganism other than that species from which the probe was derived, i.e. the probes exhibit a high degree of organism specificity. As stated, the fragments of which the probes are comprised are derived from the genomic DNA of representative organisms of a species and are cloned by known procedures into a suitable plasmid vector for amplification and subsequent isolation in sufficient quantity and purity for use in in vitro DNA-DNA hybridizations for the purposes of the invention. In preparing DNA-DNA hybridization probes for use in the invention, host bacterial cells of a well defined species of a known microorganism are propagated by conventional methods known to the art to obtain bacterial genomic DNA from the appropriately cultured bacterial cells (Lennette et al., and Parish, supra). Total bacterial genomic DNA is then isolated from the bacterial cells as by lysis of the bacteria by known techniques using combinations of enzymes, detergents and antibiotics followed by purification as by selective extraction of the cellular DNA using phenol, chloroform, isoamyl alcohol and ethyl ether. The purity of the resulting cellular genomic DNA may be established by ultraviolet spectroscopy and agarose gel electrophoresis.

The isolated bacterial genomic DNA is then subjected to digestion using restriction endonucleases, enzymes that recognize only specific nucleotide sequences as substrate. The digestion treatment produces fragments having specific base sequences and unique terminal nucleotide structures depending upon the particular restriction endonucleases employed. The terminal nucleotide structure of the fragments is important in the subsequent cloning of selected fragments into plasmid vectors.

The fragments thus produced are of various sizes depending upon the origin or source of the DNA and the restriction enzymes used in digestion. The variety of sizes of the fragments found in the enzymatically digested DNA may range from about 40 kbp to small oligonucleotides of several base pairs. Fragments of a size appropriate for use as DNA-DNA hybridization probes are selected through isolation by separation in agarose gels or sucrose density gradients. The selected fragments are isolated from the genomic DNA of the enzymatic digest as by preparative agarose gel electrophoresis.

The isolated fragments from a specific bacterial species are then enzymatically ligated into cloning sites in plasmid vectors to produce recombinant plasmids. The cloning sites in the plasmids are restriction endonuclease cleavage sites that generate specific termini complementary to the termini of the isolated fragments. By reason of this matching or fit, the fragments may be covalently inserted into the plasmids by the action of the ligation enzyme ligase.

The new recombinant plasmids thus produced are then introduced into a suitable bacterial cloning host for amplification or production of large numbers of the unique fragments which all have the same terminal nucleotide structure by virtue of having been generated by the same restriction enzymes. The introduction of the recombinant plasmids into the host bacteria is by the process of transformation, that is, the uptake of naked double stranded DNA by competent bacterial cells. Those cells that are successfully transformed are then detected on a suitable selective medium (e.g. x-Gal ampicillin agar plates) that allows the growth of only those cells that contain the recombinant plasmids. Numerous cloned fragments of the selected size (e.g. 1 kbp) are thus generated for each bacterial species. In view of the fact that the fragments were inserted into the plasmid vectors at specific restriction endonuclease sites, they can be excised by digestion of the recombinant plasmids with the same specific enzyme. This digestion leads to the production of the desired fragments which are then separated from the vector plasmids by preparative agarose gel electrophoresis, appropriately purified by repeated extractions and are then ready for use as DNA-DNA hybridization probes to detect and identify unknown bacteria or microorganisms as described below. The fragments can also be isolated and separated by a sucrose density gradient technique rather than by agarose gel electrophoresis.

Preparatory to use as DNA-DNA hybridization probes in the practice of the invention for the in vitro detection of unknown pathogens the fragments of the probes may, for example, be enzymatically labeled with radioactive phosphorous 32P using DNA polymerase I to incorporate 32P dATP into DNA using the fragments as template. The labelling of the fragments for use as probes permits their detection by autoradiography or liquid scintillation spectroscopy after hybridization to unknown target DNA preparations and thus enables one to determine whether binding of the DNA of the probes to DNA of the unknown microorganism through DNA-DNA hybridization has occurred.

In lieu of radioactive phosphorus, other radioactive elements such as radioactive sulfur ($35_S$) or iodine ($^{125}I$) may also be used as the labelling agent. Further, other forms of labelling or chemical tagging, known to the art, such as fluorescent labelling or biofluorescent labelling, may be employed. In addition, complexing or binding of a heavy metal such as mercury to the DNA of the probes followed by treatment with radioactive selenium ($75_{Se}$) and detection by scintillation spectroscopy or atomic absorption may be used for the purpose of determining whether binding of the DNA of the probes to DNA of the unknown microorganisms in the in vitro test method of the invention has occurred. Other labels which may be employed include biotin and ligands which may specifically bind to a labeled antibody, fluorescent agents, chemiluminescent agents, enzymes and the like.

Hybridization is accomplished by contacting the support carrying the fixed, single stranded pathogen DNA/RNA obtained as described with a hybridization probe having a nucleotide sequence substantially complementary to a nucleotide sequence of the pathogen DNA/RNA. The probe may be carried in a hybridization solution containing, for example, 50% formamide, 160 g/ml sheared salmon sperm DNA, 0.5 M NaCl, 0.05 M sodium citrate, and 10% dextran sulfate, the probe being present, for example, in the amount of 50 ng/ml of solution. Hybridization can be carried out by placing the support in such a hybridization probe solution contained in a plastic petri dish or other suitable vessel at 50° C. for approximately 20 to 90 minutes. Preferably, however, in accordance with the present invention, a "sandwich" technique is employed to effect hybridization. With this technique, a piece of suitable substrate such as a piece of Whatmann 3 MM filter paper (preferably cut to a dimension slightly larger than that of the support) is wetted with the hybridization solution. The support carrying the pathogen DNA/RNA is then placed on the paper and additional hybridization solution is applied. A second piece of the same paper is then placed over the support to "sandwich" the support between the two pieces of paper, and a further addition of hybridization solution is then applied. The resultant "sandwich" contained in a plastic petri dish is heated at approximately 50° C. for approximately 20 to 90 minutes, preferably 60 minutes. These particular conditions may vary for different organisms or pathogens, but may be readily empirically determined for any specific pathogen or suspected pathogen. The heating or incubation step serves the purpose of promoting the formation of more perfect hybrids and avoiding cross-reactivity. Thus, through the hybridization step, the DNA/RNA of the probe becomes bound substantially only to or reacts only with the DNA/RNA of the unknown pathogen.

Following hybridization, the support is removed and washed in a solution containing, for example, 100 ml of 1% SDS and 0.2×SSC (0.03 M NaCl, 0.003 M sodium citrate) at 73° C. for approximately 10 minutes and again in 0.2×SSC at 73° C. for approximately 10 minutes to remove unbound probe. Finally, the support is dried and counted as in a gamma counter to determine whether binding of the DNA/RNA of the probe to DNA/RNA of the unknown pathogen through hybridization has occurred. The support may be either autoradiographed by exposure to X-ray film or counted in a scintillation or other counter or both or by the other means previously mentioned which permits a ready determination to be made as to whether such binding has occurred. Labelled probe thus binds only to DNA/RNA of pathogens of the species from which the probe was generated permitting the unknown pathogen in the clinical sample to be reliably detected and identified preparatory to appropriate therapy being initiated.

Figure 2:
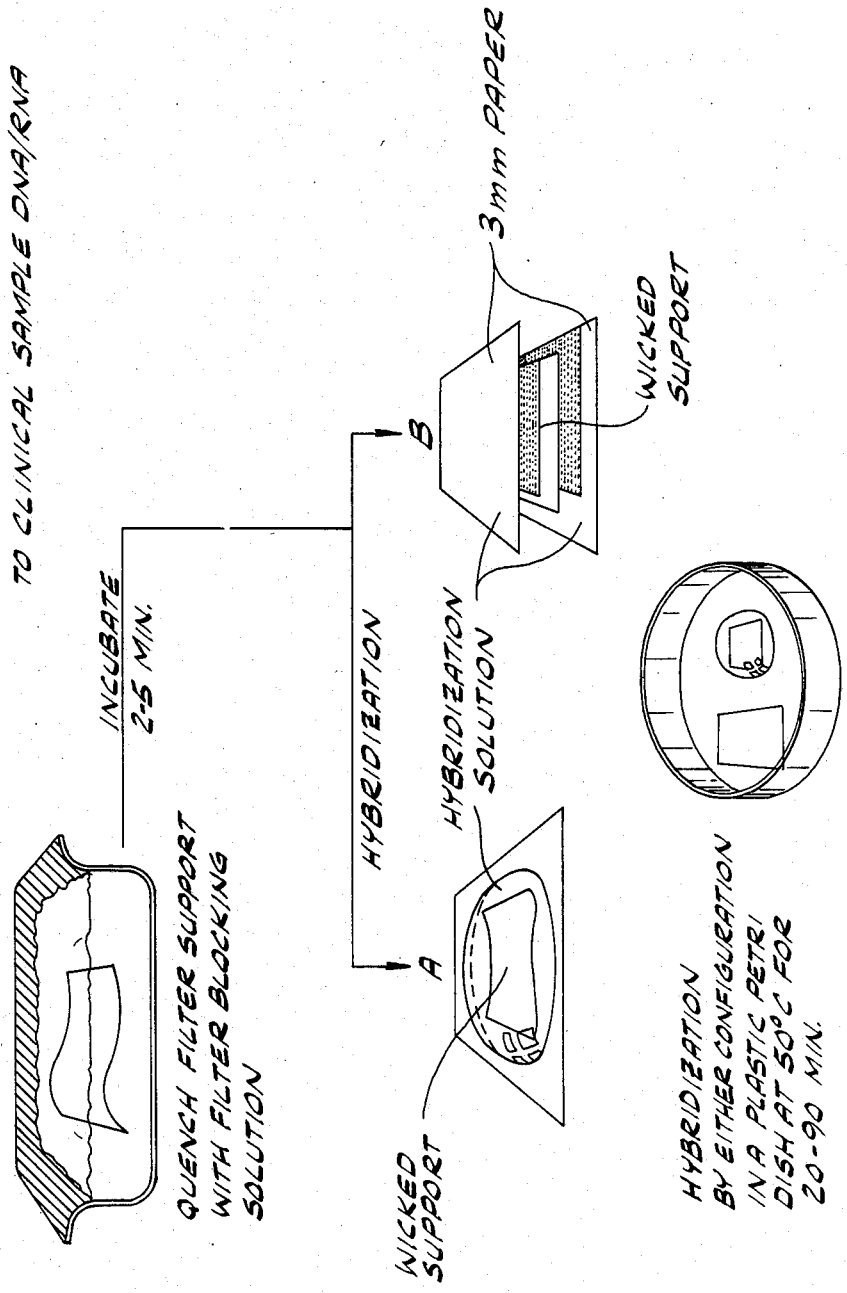
FIG. 2 is a schematic representation of the steps followed in hybridization of the probe DNA/RNA to the clinical sample DNA/RNA using the method of the invention.
Figure 3:
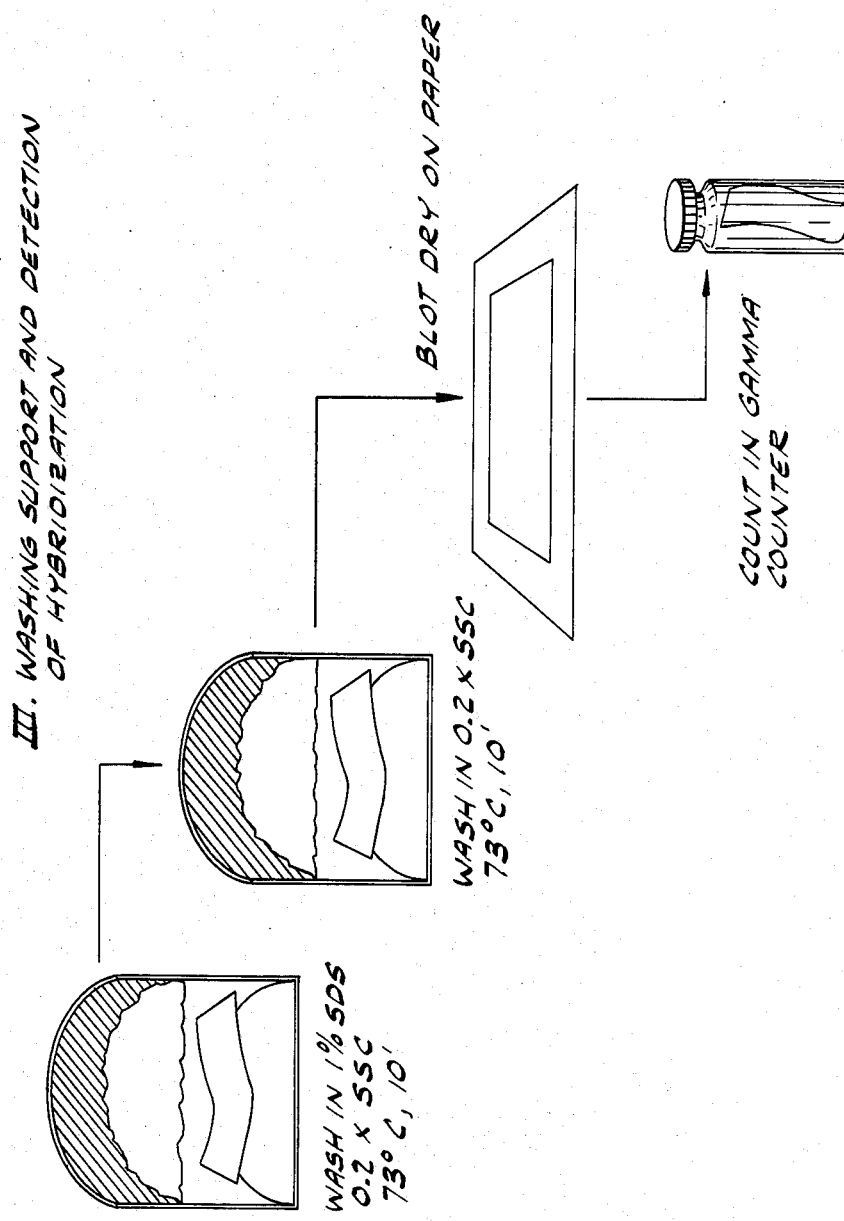
FIG. 3 is a schematic representation of the steps of washing the filter support and detecting whether hybridization has occurred in accordance with the invention.

The method of the invention as thus described in detail is shown schematically in FIGS. 1-3 of the drawings with reference to a particular sequence of the steps involved, it being understood that variations may be made, as indicated, in practicing the invention.

The present invention thus provides practical means for detecting unknown pathogens directly from clinical samples of various types, and advantageously may be practiced in a shorter period of time, i.e. as short as 1 to 2 hours, than with presently available methodology and with the desired sensitivity, precision and pathogen specificity. Also, such unknown pathogens can be detected at concentrations below those required for detection by conventional methods.

The present invention is broadly applicable to the detection of any pathogen or organism which contains nucleic acid (i.e. DNA or RNA), and as used herein, the expression DNA/RNA means DNA and/or RNA. Such pathogens or organisms include, as illustrative examples, Escherichia coli, Streptococcus fecalis(Streptococcus-Group D), Staphylococcus aureus, Pseudomonas aeruginosa, Streptococcus-Group A, Streptococcus pneumoniae, the yeast Candida albicans, Haemophilus influenzae, Klebsiella pneumoniae, Proteus Mirabilis, Proteus vulgaris, Serratia marcescens, Peptostreptococcus anerobius, Clostridium perfringens, Propionibacterium SP, Bacteroides fragilis and other known gram positive and gram negative cocci, bacilli and yeast or fungi. Also included are viruses such as the Herpes simplex virus Type II.

In those instances where it is deemed necessary, the bacterial cell density of the clinical specimen employed may be increased by incubation on an appropriate growth substrate for a period of up to 8 hours.

The following are illustrative procedures for the preparation of specific DNA-DNA hybridization probes for use in the practice of the invention.

1. Isolation and purification of genomic DNA from selected bacteria species.

DNA from clinically significant bacterial and fungal species such as Escherichia coli was isolated from overnight broth cultures of the microorganisms by enzymatic, detergent and/or antibiotic lysis procedures. The preparation of Escherichia coli genomic DNA as described herein may, with minor variations, also be used to isolate DNA from other microorganisms or pathogens.

Cells from a 1 liter overnight broth culture were washed in 60 ml, 150 mM NaCl, 10 mM EDTA, pH 8.0. The cells were then sedimented by centrifugation and resuspended in 15 ml, 30 mM NaCl, 2 mM EDTA, pH 8.0. Ten mg of lysozyme was added and the mixture was incubated at 37° C. for 30 minutes. After incubation, 0.4 ml 5M NaCl, 0.2 ml 0.5 M EDTA and 2.0 ml of 20% SDS (sodium dodecyl sulfate) were added. This mixture was heated for 15 min at 60° C. and then cooled to room temperature. Six ml of 5 M $NaClO_4$ was added and the mixture then repeatedly extracted with an equal volume of $CHCl_3$: isoamyl alcohol (24:1). The aqueous phase was collected and the DNA precipitated with 2.5 volumes of cold (−20° C.) 95% ethanol. The DNA precipitate was then dissolved in 0.1×TNE (50 mM Tris-HCl, pH 7.5, 100 mM NaCl, 5 mM EDTA). RNase was added to a final concentration of 20 g/ml followed by incubation at 37° C. for one hour. The DNA preparation was then extracted with phenol: $CHCl_3$: isoamyl alcohol (25:24:1), then precipitated with 2.5 volumes cold 95% ethanol.

Figure 4:
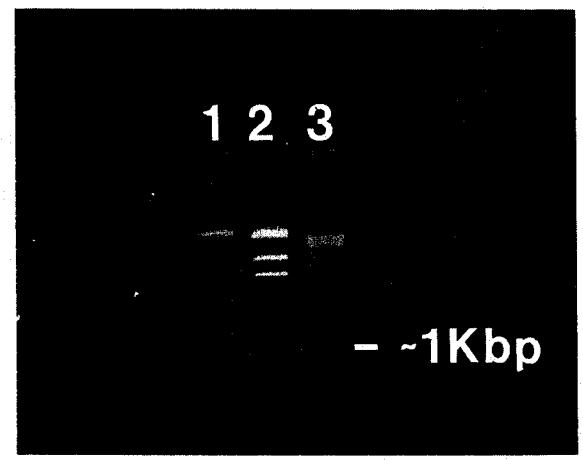
FIG. 4 depicts the results of an agarose gel electrophoretic analysis of bacterial genomic DNA.

In FIG. 4 is shown agarose gel electrophoresis of bacterial genomic DNA prepared as described above. In lane 1 of FIG. 1": 100 ng of purified genomic DNA prepared as described; in lane 2: Hind III endonuclease digest of bacteriophage DNA used as size markers. The doublet bands 5 and 6 from the top are 2.2 and 2.1 kb pairs, respectively; in lane 3: Hind III complete digest of genomic DNA. On similar preparative gels, the area containing approximately 1 kb genomic fragments in the complete digest was excised and the DNA from that area recovered as further described below.

2. Isolation of bacterial DNA genomic fragments of approximately 1 kilobase (kbp) size.

Purified bacterial genomic DNA from above was then treated with appropriate restriction endonucleases in order to generate fragments for incorporation into a bacterial plasmid cloning vector. Genomic fragments of ~1 kbp were selected as hybridization probe DNA and purified fragments isolated as described below were cloned into cloning vector plasmid pUC9.

Purified E. coli DNA was completely digested with restriction endonuclease Eco Rl. The digest was electrophoresed in a 0.5% low melting temperature agarose gel for 2 hours at 80 volts at 4° C. Areas of the gel corresponding to the 1 kbp region were excised and the DNA recovered by heating the agarose at 60° C. for 30 minutes, followed by extraction with phenol saturated with 10 mM Tris, 1 mM EDTA at pH 8.0.

Figure 5:
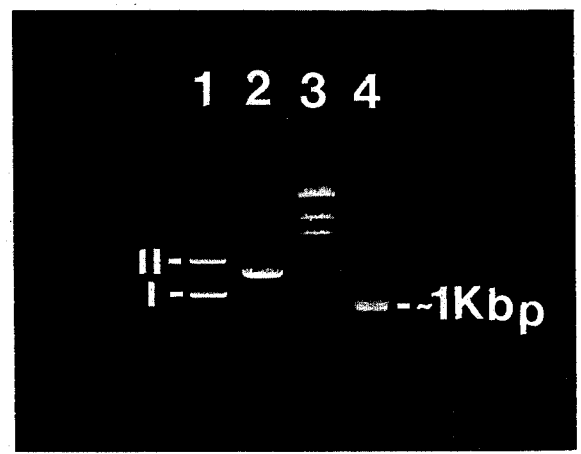
FIG. 5 depicts the results of an agarose gel electrophoretic analysis of cloning vector plasmid pUC9 and recovered genomic fragments of approximately 1 kb in size.

In FIG. 5 is shown agarose gel electrophoresis of cloning vector plasmid pUC9 and recovered genomic fragments of approximately 1 kbp. In lane 1 of FIG. 5: purified plasmid pUC9. The several bands seen represent the super coiled (Form I), open circle (Form II) and multimeric forms of each; in lane 2: plasmid pUC9 that has been made linear (Form III) by the action of Hind III as described below. The linearized plasmid may then be enzymatically recombined with the genomic fragments (shown isolated and purified in lane 4) to give recombinant plasmids; Lane 3: Hind III digest of DNA.

3. Construction of recombinant plasmids containing bacterial genomic DNA.

Purified bacterial genomic DNA fragments were ligated into linearized plasmid pUC9 at the Eco Rl, Hind III or Pst I restriction site. Ligation reactions were carried out by mixing the plasmid and fragment at a molar ratio of 1:3, followed by coprecipitation of the DNA'S in 95% ethanol. The precipitated DNA mixture was then resuspended in 2.4 $\mu$l of 10 mM Tris, 1 mM EDTA and the following reagents added: 0.4 $\mu$l 1 100 mM dithiothreitol, 0.4 $\mu$l 10 mM ATP, 0.4 $\mu$l 1 10 reannealing buffer (50 mM Tris pH 8.0, 7.5 mM $MgCl_2$, 0.02% gelatin) and 0.4 $\mu$l (1.0 unit/$\mu$l) T4 ligase. The ligation mixture was incubated at 15° C. for 14 hours and then the reaction was stopped by the addition of EDTA. The mixture was extracted once with phenol: $CHCl_3$: isoamyl alcohol and the ligated DNA precipitated with 95% ethanol. The DNA precipitate containing the recombinant plasmids was dissolved in 5 $\mu$l of 10 mM Tris, 1 mM EDTA and used to transform competent bacterial host E. coli JM 83.

4. Bacterial transformation: Cloning of recombinant plasmids.

E. coli strain JM 83 was made competent for transformation by treatment in $CaCl_2$. A rapidly growing broth culture of JM 83 was grown to $OD_{590=0.2}$. Twenty ml of the culture was centrifuged at 4° C., 6 minutes at 6000 RPM and the cell pellet was resuspended in 20 ml of cold 0.1 m $CaCl_2$. The cell suspension was kept on ice for 20 minutes, centrifuged in the cold and the cells resuspended in 0.5 ml of fresh cold 0.1 M $CaCl_2$. Fifty $\mu$l of the cell suspension was then mixed with 5$\mu$l of the recombinant plasmid solution from the previous ligation reaction. The transformation mixture was kept on ice an additional 10 minutes and then brought to 37° C. for 5 minutes. Warm (37° C.) LB broth (10 g tryptone, 5 g yeast extract, 10 g NaCl/liter of the LB broth) was added to bring the volume to 1.5 ml and this suspension was incubated at 37° C. for 30 minutes. The mixture was centrifuged to sediment the cells which were then resuspended in 200 $\mu$l fresh LB broth and spread on the surface of selective X-Gal agar plates containing 100$\mu$g/ml ampicillin. The plates were incubated overnight at 37° C. Transformant colonies which contained recombinant plasmids were identified by their growth as white colonies on the X-gal medium (X-gal medium/liter: 10g tryptone, 5 g yeast extract, 0.5 g NaCl, 1.0 ml 2N NaOH, 2.5 ml 2% X-Gal in N,N-dimethylformamide). Numerous transformants each with a recombinant plasmid containing genomic DNA from Staphylococcus aureus, Streptococcus fecalis, Pseudomonas aeruginosa or Escherichia coli were isolated.

Figure 6:
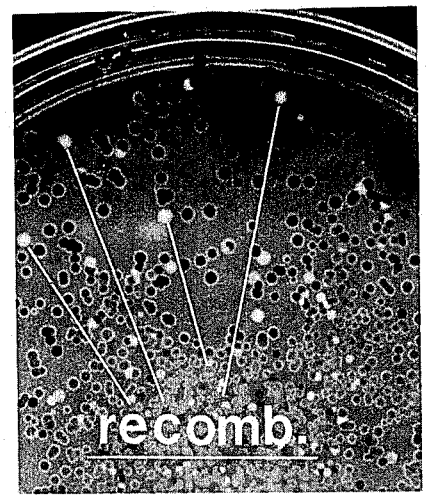
FIG. 6 is a photograph showing or illustrating the selection of transformed bacterial cells containing recombinant plasmids.

FIG. 6 is a photograph which is illustrative of the selection of transformed bacterial cells containing recombinant plasmids. Bacterial clones harboring plasmids constructed to contain bacterial genomic inserts are seen as white colonies. The dark colonies also contain restructured plasmid pUC9 but without genomic inserts. The color difference which allows identification of recombinant plasmids is a result of the inactivation of a lactose fermentation gene into which the foreign DNA fragment has been inserted. The transformants were selected on X-Gal medium containing ampicillin.

Transformants containing recombinant plasmids were subcultured to X-Gal, ampicillin plates and the recombinant plasmids were extracted and analyzed by restriction endonuclease digestion and agarose gel electrophoresis. Clones containing recombinant plasmids were selected for further development on the basis of the presence of a single genomic insert, readily excised from the plasmid by restriction endonuclease digestion. Those clones selected were subcultured, the recombinant plasmids extracted, and the bacterial genomic inserts excised and purified by electrophoresis in low melting temperature agarose. The inserts to be used as hybridization probes were further purified by phenol extraction and ethanol precipitation in preparation for 32p labelling by nick translation.

Figure 7:
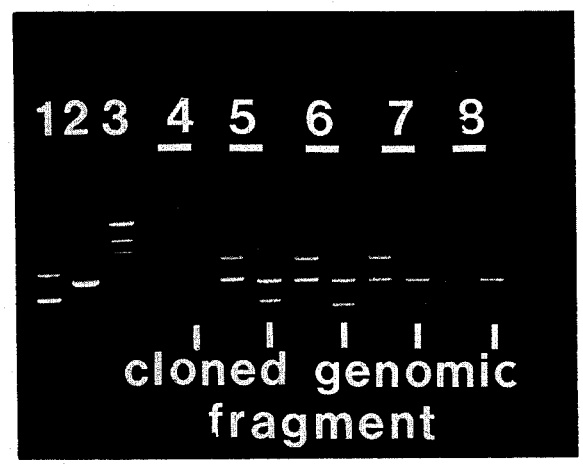
FIG. 7 depicts the results of an agarose gel electrophoretic analysis of recombinant plasmids recovered from transformed bacteria.

In FIG. 7 is shown the agarose gel electrophoretic analysis of recombinant plasmids recovered from transformed bacteria. Plasmid DNA from transformants was extracted, purified and digested with an appropriate restriction endonuclease in order to recover the amplified cloned genomic fragments to be used as species specific probes. There is shown in Lane 1, plasmid pUC9; Lane 2, plasmid pUC9 in its 2.7 kbp linear form following Hind III digestion; Lane 3, $\lambda$ Hind III size markers. The remaining lanes (pairs designated 4 through 8) show recombinant plasmids containing cloned bacterial genomic fragments. The first lane of each pair shows the purified recombinant plasmid while the second lane of the pair shows the same plasmid after digestion with Hind III. Such digestion excised the cloned genomic fragment which can be clearly seen as the bottom-most band in the lane. The upper band is the linearized (form III) plasmid vector. Comparison of migration distance of the intact recombinant plasmids (the first lane of each pair) with the vector plasmid pUC9 in Lane 1 clearly indicates the recombinant plasmids are larger. Also, comparison of the excised cloned genomic fragments show each of them to be different. Clones to be used as species specific hybridization probes were initially screened in this manner.

5. Preparation of 32p labeled hybridization probes.

Nick translation labeling of purified cloned bacterial genomic fragments was done by a known protocol provided by Bethesda Research Labs. Following 32p labeling of the DNA, unincorporated label was removed by column chromatographic purification of the ~1 kbp DNA molecule through a column containing Sephadex G-50 in 0.2 M NaCl, 10 mM Tris pH 7.6 and 0.5 mM EDTA. The nick translation reaction mixture was passed through the column followed by successive 50 $\mu$l elutions of 10 mM Tris, 1 mM EDTA. Each fraction was assayed for radioactivity using a scintillation counter and that fraction which contained the maximum acid precipitable label was saved as a hybridization probe.

Figure 8:
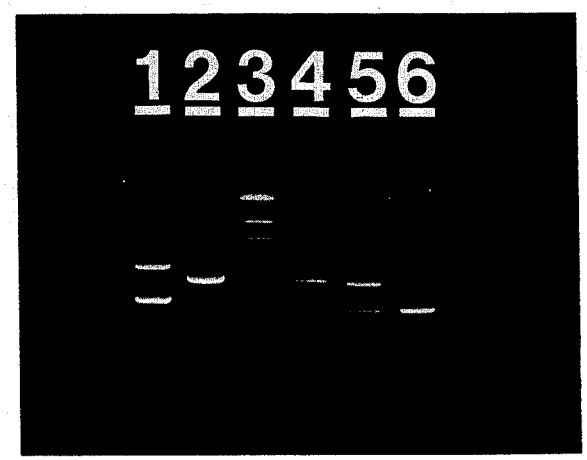
FIG. 8 depicts the results of an agarose gel electrophoretic analysis of a cloned genomic fragment for use as a hybridization probe in the practice of the present invention.

FIG. 8 shows agarose gel electrophoresis of a cloned genomic fragment for use as a hybridization probe. The excision of the cloned genomic fragment from selected recombinant plasmids using restriction endonucleases was then followed by the separation and purification of the fragment which was subsequently labeled with 32p and used as a hybridization probe reagent to identify unknown bacteria. FIG. 8 shows one of the resultant cloned fragments used in this procedure. Lanes 1, 2 and 3, respectively, contain cloning vector pUC9, linearized pUC9 and λDNA-Hind III digest. Lane 4 is recombinant plasmid pSA7 (PUC9 with a *S. aureus* genomic insert). Lane 5, pSA7 after digestion with Hind III. Lane 6, the cloned *S. aureus* genomic insert from pSA7.

6. Practice of the Invention

Figure 9:
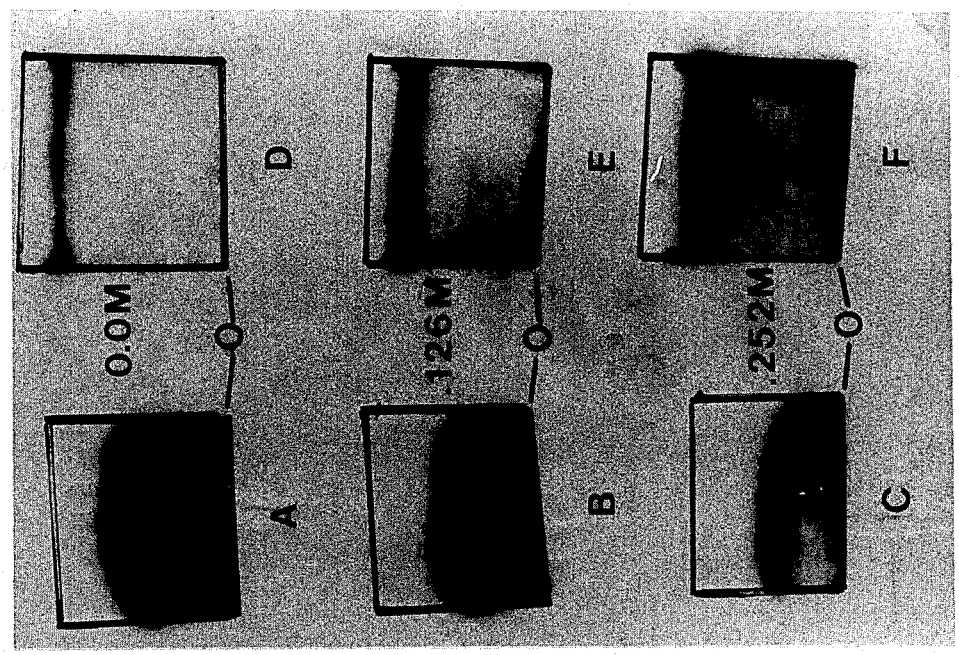
FIG. 9 shows a series of autoradiographs designated A through F obtained with lysis solution containing 500 ng GABHS DNA at different NaCl concentrations wicked onto GeneScreen supports (A-C) and nitrocellulose (D-F) and hybridized.

Lysis solution (126 mM sodium chloride, 8mM ethylene diaminetetra acetate, 10 mM Tris, pH 7.5, and 2.35% SDS made 0.5 N in sodium hydroxide) containing 500 ng of purified Group A, beta-hemolytic streptococci (GABHS) DNA was wicked onto both GeneScreen and nitrocellulose filter supports at various salt concentrations to test for hybridization. NaCl concentrations of 0.0M, 0.126M, and 0.256M were used. The DNA probe used for hybridization was prepared as described above and represented approximately 1/4000 of the GABHS chromosomal DNA, and was labelled to a specific activity of $3 \times 10^8$ cpm/μg. Hybridization was done for one hour at 51° C., followed by a wash at 73° C. in 1% SDS, 0.2×SSC for 10 min, and a final wash at 73° C. in 0.2×SSC for 10 min. The filter supports were then autoradiographed on X-ray film using an intensifying screen. The autoradiograph is shown in FIG. 9 ("O" designating the point of origin).

The autoradiograph indicated three characteristics: first, the effect of NaCl on reactivity depends upon the support employed for the wicking. With the GeneScreen support, the lower salt concentration yields better reactivity. Conversely, increasing salt enhances reactivity when using nitrocellulose, most likely due to increased binding of substrate DNA to the support due to the ionic environment produced when the salt is present. Second, the position on the GeneScreen support of the SDS front relative to the origin and water front varies according to the concentration of NaCl present. The less salt, the further the SDS front migrates. Third, conditions exist whereby either matrix or support can be made comparable for their ability to serve as wicking substrates or materials. Thus, nitrocellulose used with 0.256M NaCl in the lysis solution is comparable in reactivity to the GeneScreen support used with minimal salt in the lysis solution. It should also be noted that an obvious SDS front does not form when nitrocellulose is used as the support material, the DNA being located just below the solvent front, whereas with the GeneScreen support, the DNA is located directly above the SDS front.

Figure 10:
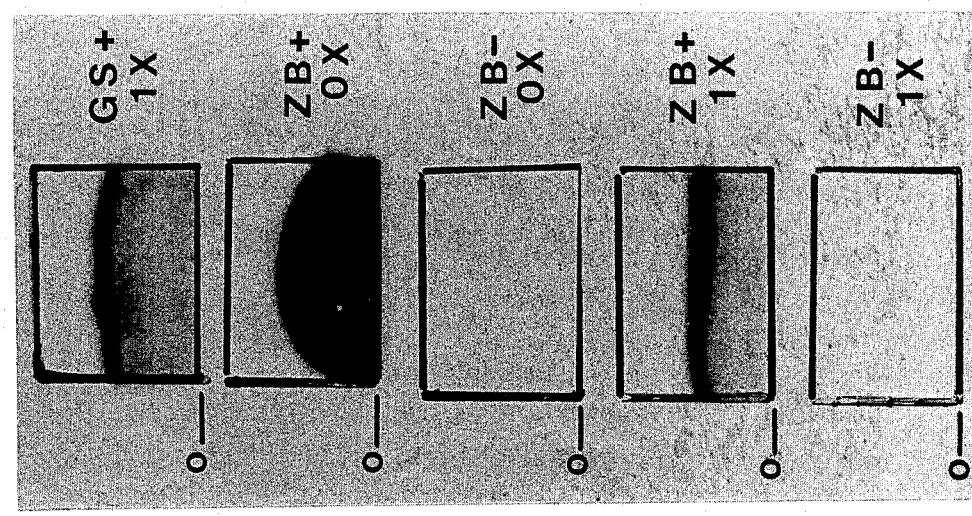
FIG. 10 shows a series of autoradiographs demonstrating the similarity of function in the practice of the invention of Zetabind and GeneScreen as support materials.

A third support matrix, Zetabind, was also tested for its ability to function similarly to GeneScreen. Purified GABHS DNA was seeded into lysis solution (2.35% SDS, 0.5N NaOH) containing zero and 0.126M NaCl. Aliquots were wicked onto both GeneScreen and Zetabind supports, and the filters were hybridized to a GABHS-specific DNA probe. The supports were autoradiographed and counted and the results are shown in FIG. 10 ("OX" standing for 0.0M NaCl, "IX" standing for 0.126M NaCl, "GS" standing for GeneScreen and "ZB" standing for Zetabind).

The results indicate that GeneScreen and Zetabind function in a similar manner. First, an SDS front is identified with both supports. Second, the majority of reactivity upon hybridization is easily identified as immediately past the SDS front. Third, based upon the counts obtained by liquid scintillation counting, the amount of hybridization that occurred is quantitatively similar. Also, as shown previously for the GeneScreen support, minimal salt concentrations produced optimum reactivity with Zetabind.

Using a GeneScreen support, a determination was made of the effect of the wicking support dimensions on hybridization reactivity. Purified GABHS DNA was seeded into 50μl of lysis solution containing an aliquot of pooled material eluted from recently obtained throat swabs. Two sets of GeneScreen supports were used: one set was 6 mm in width and a second set was 12 mm at the base that tapered up to a width of 18 mm. Both sets were large enough to accommodate the total volume of lysis solution to be wicked. After the DNA-containing solution was wicked, both sets of supports were hybridized in the same hybridization solution. The supports were washed, autoradiographed and counted. The results are shown in FIG. 11.

Figure 11:
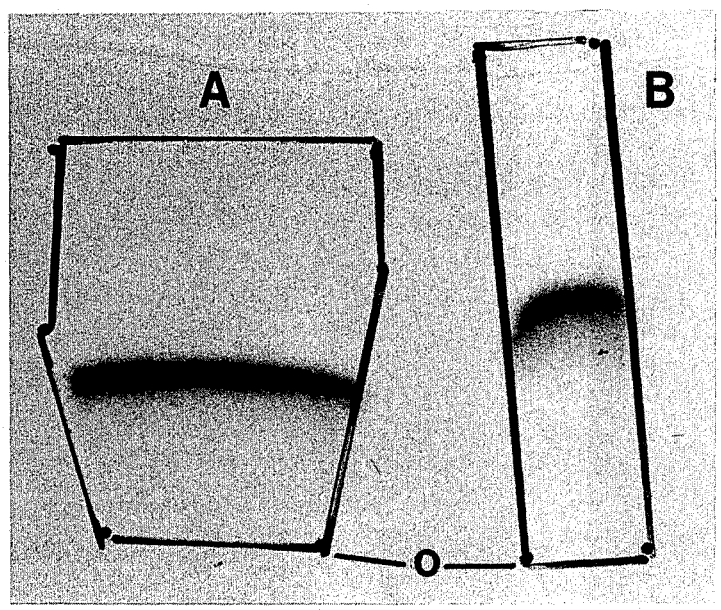
FIG. 11 shows two autoradiographs designated A and B demonstrating the effect of the wicking support dimensions on hybridization reactivity.

The results indicate that reactivity can be enhanced by up to 50% if the wider wicking support is used (see A vs. B in FIG. 11).

The utility of wicking lysed cellular material directly from clinical samples was tested using three types of clinical samples, namely, throat swabs, urine and vaginal swabs.

Patients suspected of having pharyngitis were cultured with duplicate swabs. For isolation of Group A, beta-hemolytic streptococci (GABHS) to compare the DNA hybridization technique of the present invention with standard assays, one of the swabs was used for culturing on a blood agar plate. A bacitracin sensitivity disc was placed in the primary and secondary streak areas of the plate for the differentiation of GABHS from non-group A streptococci. A zone of inhibited growth around the disc, in addition to the presence of beta-hemolytic streptococci on the plate, resulted in the identification of a positive culture. Some primary plates had small numbers of betahemolytic streptococcal colonies, but failed to display an obvious zone of inhibited growth around the disc. Representative colonies from these plates were subcultured and their sensitivity to bacitracin reevaluated.

Figure 13:
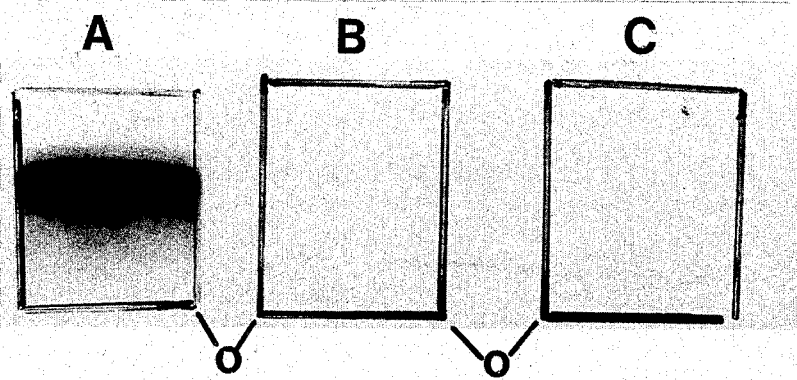
FIG. 13 shows three autoradiographs or X-ray photographs, the one designated A showing a positive detection of GABHS in throat swab material and those designated B and C showing negative results.

The second swab of each pair was used for DNA hybridization analysis. Throat swab material was eluted directly into a pre-lysis solution of the composition previously described and collected by centrifugation. This pellet of material was resuspended in the above-noted lysis solution which effectively lysed the bacteria present and liberated the nucleic acids from within these cells. Cell debris was removed from the solution by centrifugation. The resulting supernatant was wicked onto a solid, inert, porous support, GeneScreen or nitrocellulose, and the support was subsequently hybridized to a GABHS-specific DNA probe that was labelled with radioactive phosphorous. Detection of hybridization was by autoradiography. Representative results from these experiments with a GeneScreen support are shown in FIG. 13, the X-ray photograph on the left designated A showing a positive detection and the other two X-ray photographs designated B and C showing negative results.

Of the 119 patients tested, standard assay procedures indicated that there were 65/119 positive for GABHS. Using the method of the present invention, 63/119 were found to be positive. The two discrepancies between the techniques were with cultures that had beta-hemolytic streptococci that exhibited sensitivity to bacitracin on primary cultures. Upon subculturing and typing, the beta-hemolytic streptococci from these two isolates were determined to be group C streptococci.

The same method described above was used to examine urine for the presence of *Escherichia coli*, using a radioactively labelled *E. coli*-specific probe. Cells were lysed with the same alkali SDS lysis solution, wicked directly onto a GeneScreen support and the support then hybridized. The autoradiographs indicated that with this type of body fluid, the pathogen is readily lysed and the pathogen nucleic acid readily wicked onto a support in hybridizable form, the autoradiographs clearly distinguishing between positive and negative results.

Figure 12:
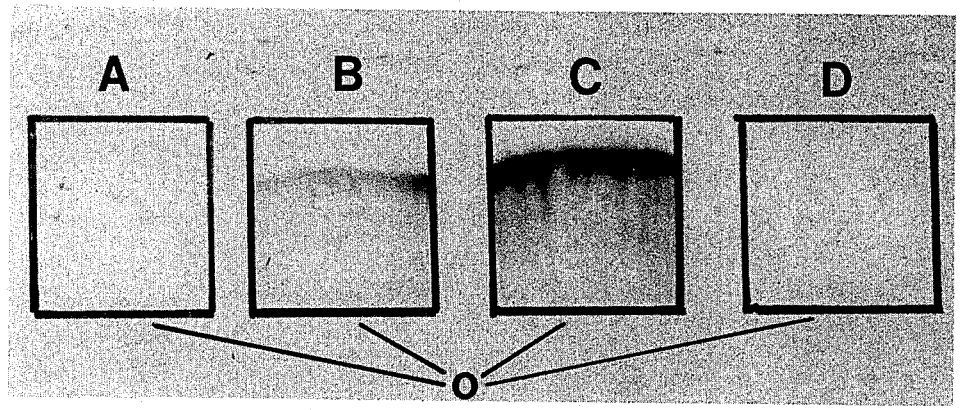
FIG. 12 shows four autoradiographs of DNA hybridization analysis of our clinical vaginal swabs, those designated A and D showing negative results and those designated B and C showing positive results.

The method of the invention has also been used to detect the presence of *Herpes simplex* virus Type II in vaginal swabs. Representative autoradiographs of such hybridizations are shown in FIG. 12, those designated A and D showing negative results and those designated B and C showing positive results. 7. Identification of Group A β-hemolytic Streptococcus in Clinical throat specimens.

The identification of Group A β-hemolytic *Streptococcus pyogenes* from throat swabs is required before a diagnosis of streptococcal pharyngitis can be established. The following is an example of the practice of the invention for identification of Group A β-hemolytic streptococcus using actual patient clinical specimens.

Collection of patient specimens was by the standard procedure, i.e., the posterior pharynx and tonsillar area was vigorously swabbed with a sterile fiber tipped applicator. The swabs were then processed as follows:

1. The swab was vigorously agitated by hand in 400 μl of 10 mM Tris pH 7.5, contained in a 1.5 ml polypropylene centrifuge tube.

2. The material eluted from the swab was then sedimented by centrifigation for 30 seconds (15.600xG) in an Eppendorf centrifuge.

3. The supernatant was aspirated using a pasteur pipette. The supernatant was discarded.

4. The pellet was then resuspended in 50μl of rapid lysis solution (10 mM Tris, pH 7.5, 12.6 mM NaCl, 8 mM EDTA, 2.35% SDS, made 0.5N NaOH by addition of 10 N NaOH), and vigorously agitated using a vortex mixer for 10 seconds.

5. The lysate preparation was centrifuged for 30 seconds in the Eppendorf centrifuge and the 50μl supernatant collected in a micropipette tip for application to the solid DNA binding matrix (marketed under the trade designation "Genescreen Plus").

6. The 50 μl lysate was applied to an approximately 20 mm square of the positively charged DNA binding matrix ("Genescreen Plus") by placing the liquid on a nonwettable surface such as parafilm and bringing the liquid drop in contact with the edge of the DNA binding matrix, in such a way to cause the liquid to be absorbed by capillary action.

7. The wetted 20 mm square of DNA binding matrix was then allowed to air dry for several minutes.

8. The dried matrix was then submerged for several seconds in quenching solution (0.2% polyvinylpyrollidone, M.W. 360,000, 0.2% bovine serum albumin, 0.2% Ficoll, M.W. 400,000).

9. Excess quenching solution was drained from the 20 mm square and the square placed on the surface of a 30×30 mm piece of Whatman 3 MM filter paper saturated with hybridization solution* containing 20 ng of 32p labelled GpA specific hybridization probe DNA/ml. A second 30×30 MM Whatman filter paper was placed on top of the 20×20 square of DNA binding matrix and then saturated with additional hybridization solution.

*Hybridization solution—formamide 40% v/v 4 x SSC (0.15M NaCl 0.015M Na citrate)
Sheared denatured salmon Sperm DNA 200μg/ml Dextran sulfate 10% v/v 10. The sandwich of filter paper and DNA binding matrix contained in a 100 mm disposable plastic petri dish was floated on the surface of water at 50° C. for 1 hour.

11. After the 1 hr incubation, the DNA binding matrix was recovered and washed in 1% SDS, 0.2×SSC* for 10 min at 73° C., then in 0.2×SSC for 5 min.

12. After washing, the 20×20 mm square of DNA binding matrix was autoradiographed for 1 hr at −100° for a permanent record and then counted in a liquid scintillation counter.

The results of typical tests for group A β-hemolytic streptococci are shown in the autoradiographs in FIG. 13. Radioactive counts were then determined for each of the test squares in FIG. 13. The values as counts per minute for A, B and C respectively were 1971, 89 and 92. These findings are typical of clinical specimens tested by the method of the invention.

In view of the above, it will be seen that the several objects of the invention are achieved and other advantageous results attained.

As various changes could be made in the above products and methods without departing from the scope of the invention, it is intended that all matter contained in the above description or shown in the accompanying drawings shall be interpreted as illustrative and not in a limiting sense.

What is claimed is:

1. In a method for the in vitro detection of an unknown genetic entity having a specific DNA and/or RNA nucleotide sequence present in a sample suspected of containing said genetic entity wherein the DNA and/or RNA is liberated from said sample in single stranded form and deposited on a support, the improvement which comprises the steps of (a) contacting a solution containing said liberated sample DNA and/or RNA, an alkali and an anionic or zwitterionic surface active agent with a porous, inert, positively charged support whereby said solution migrates by capillary action on said support and said sample DNA and/or RNA in single stranded form becomes affixed at areas on said support to which the sample DNA and/or RNA has migrated;

(b) contacting the resulting support carrying said fixed single stranded sample DNA and/or RNA with a hybridization probe having a nucleotide sequence substantially complementary to a nucleotide sequence of said sample DNA and/or RNA whereby through hybridization the DNA and/or RNA of said probe becomes bound substantially only to the DNA and/or RNA of the unknown sample; and (c) detecting the presence of said unknown DNA and/or RNA by determining whether binding of the DNA and/or RNA of said probe to DNA and/or RNA of the unknown sample through hybridization has occurred.

2. A method as set forth in claim 1 wherein said alkali is sodium hydroxide and said anionic or zwitterionic surface active agent is selected from the group consisting of sodium dodecyl sulfate, sodium decyl sulfate, sodium tetradecyl sulfate, sodium dodecanoate, sodium cholate, sodium deoxycholate, lyso phosphatidylcholine, N-dodecyl betaine, N-tetradecyl betaine, N-hexyl-N,N-dimethyl-3-ammonio-1-propanesulfonate, N-octyl-N,N-dimethyl-3-ammonio-1-propenesulfonate, N-decyl-N,N-dimethyl-3-ammonio-1-propanesulfonate, N-dodecyl-N,N-dimethyl-3-ammonio-1-propanesulfonate, N-tetradecyl-N,N-dimethyl-3-ammonio-1-propanesulfonate and N-hexadecyl-N,N-dimethyl-3-ammoniol-propanesulfonate.

3. A method as set forth in claim 2 wherein said anionic surface agent is sodium dodecyl sulfate.

4. A method as set forth in claim 1 wherein said support is positioned at an angle in contacting it with said solution in step (a) for a sufficient time for all of said solution to be absorbed by said support.

5. A method as set forth in claim 4 wherein said support is thereafter air dried to irreversibly affix said sample DNA and/or RNA to said support.

6. A method as set forth in claim 5 wherein the resulting support is treated to substantially reduce nonspecific binding of nucleic acids to said support during step (b).

7. A method as set forth in claim 1 wherein said probe is labelled with a radionuclide.

8. A method as set forth in claim 1 wherein said probe is labelled with a fluorescent molecule 9. A method as set forth in claim 1 wherein the binding of the DNA and/or RNA of said probe to DNA and/or RNA of the unknown sample through hybridization is determined through the use of an antibody-enzyme complex.

10. A method as set forth in claim 1 wherein the binding of the DNA and/or RNA of said probe to DNA and/or RNA of the unknown sample through hybridization is determined through the use of an antibody-fluorescent molecule complex.

11. A method as set forth in claim 1 wherein the binding of the DNA and/or RNA of said probe to DNA and/or RNA of the unknown sample through hybridization is determined through the use of chemiluminescence.

12. A method as set forth in claim 1 wherein said resulting support in step (b) is sandwiched between two solid members impregnated with a hybridization solution containing said hybridization probe to effect said hybridization.

13. A method for the in vitro detection of the presence of an unknown pathogen in a clinical sample suspected of containing said pathogen comprising the steps of (a) lysing said pathogen in said sample with an aqueous lysis solution containing an alkali and an anionic or zwitterionic surface active agent to liberate the DNA and/or RNA of said pathogen into said lysis solution in single stranded form;

(b) contacting the resulting lysis solution containing the pathogen lysate with a porous, inert, positively charged support having DNA-binding capacity whereby said lysis solution migrates by capillary action on said support and said pathogen DNA and/or RNA in single stranded form becomes affixed at areas on said support to which the pathogen DNA and/or RNA has migrated;

(c) contacting the resulting support carrying said fixed single stranded pathogen DNA and/or RNA with a hybridization probe having a nucleotide sequence substantially complementary to a nucleotide sequence of said pathogen DNA and/or RNA whereby through hybridization the DNA and/or RNA of said probe becomes bound substantially only to the DNA and/or RNA of the unknown pathogen; and (d) detecting the presence of said unknown pathogen by determining whether binding of the DNA and/or RNA of said probe to DNA and/or RNA of the unknown pathogen through hybridization has occurred.

14. A method as set forth in claim 13 wherein said sample is initially cultivated to produce more pathogen DNA and/or RNA.

15. A method as set forth in claim 13 wherein support is nitrocellulose.

16. A method as set forth in claim 13 wherein said pathogen is a virus.

17. A method as set forth in claim 13 wherein said probe codes for an excreted product.

18. A method as set forth in claim 13 wherein said probe codes for a cytoplasmic product.

19. A method as set forth in claim 13 wherein said probe is labelled with a radionuclide.

20. A method as set forth in claim 13 wherein said probe is labelled with a fluorescent molecule.

21. A method as set forth in claim 13 wherein the binding of the DNA and/or RNA of said probe to DNA and/or RNA of the unknown pathogen through hybridization is determined through the use of an antibody-enzyme complex.

22. A method as set forth in claim 13 wherein the binding of the DNA and/or RNA of said probe to DNA and/or RNA of the unknown pathogen through hybridization is determined through the use of an antibody-fluorescent molecule complex.

23. A method as set forth in claim 13 wherein the binding of the DNA and/or RNA of said probe to DNA and/or RNA of the unknown pathogen through hybridization is determined through the use of chemiluminescence.

24. A method as set forth in claim 13 wherein said hybridization in step (c) is carried out at approximately 50° C. for about 20 to 90 minutes.

25. A method as set forth in claim 13 wherein said resulting support in step (c) is sandwiched between two solid members impregnated with a hybridization solution containing said hybridization probe to effect said hybridization.

26. A method as set forth in claim 13 wherein said alkali is sodium hydroxide and said anionic surface active agent is selected from the group consisting of sodium, dodecyl sulfate, sodium decyl sulfate, sodium tetradecyl sulfate, sodium dodecanoate, sodium cholate and sodium deoxycholate, lyso phosphatidylcholine, N-dodecyl betaine, N-tetradecyl betaine, N-hexyl-N,N-dimethyl-3-ammonio-1-propanesulfonate, N-octyl-N,N-dimethyl-3-ammonio-1-propenesulfonate, N-decyl-N,N-dimethyl-3-ammonio-1-propanesulfonate, N-dodecyl-N,N-dimethyl-3- ammonio-1-propanesulfonate, N-tetradecyl-N,N-dimethyl-3-ammonio-1-propanesulfonate and N-hexadecyl-N,N-dimethyl-3-ammoniol-propanesulfonate.

27. A method as set forth in claim 26 wherein said anionic surface active agent is sodium dodecyl sulfate.

28. A method as set forth in claim 13 wherein said pathogen is a unicellular organism.

29. A method as set forth in claim 28 wherein said pathogen is a bacterium.

30. A method as set forth in claim 13 wherein said support is positioned at an angle in contacting it with said resulting lysis solution in step (b) for a sufficient time for all of said solution to be absorbed by said support.

31. A method as set forth in claim 30 wherein said support is thereafter air dried to irreversibly affix pathogen DNA and/or RNA to said support.

32. A method as set forth in claim 31 wherein the resulting support is treated to substantially reduce non-specific binding of nucleic acids to said support during step (c).

33. A method as set forth in claim 13 wherein prior to step (a) said smaple is treated to substantially remove competing or inhibiting components from the pathogen DNA and/or RNA of said sample without lysing said pathogen.

34. A method as set forth in claim 33 wherein said competing or inhibiting components are removed from the DNA and/or RNA of said pathogen by eluting said pathogen into an aqueous pre-lysis solution that does not lyse said pathogen.

35. A method as set forth in claim 34 wherein said pathogen is collected by centrifugation, filtration or evaporation of said aqueous solution.

36. A method as set forth in claim 33 wherein said sample is treated with a pre-lysis solution containing an enzyme to enhance lysis of said pathogen at temperatures between approximately 15° C.–75° C. for incubation periods of up to approximately 60 minutes.

37. A method as set forth in claim 36 wherein said enzyme is capable of hydrolyzing protein.

38. A method as set forth in claim 36 wherein said enzyme is capable of solubilizing lipid.

* * * * *